(12) United States Patent  
Maulard

(10) Patent No.: US 8,212,204 B2
(45) Date of Patent: Jul. 3, 2012

(54) CALIBRATED FLEXIBLE RADIOACTIVE SOURCE

(75) Inventor: Alain Maulard, Champs sur Marne (FR)

(73) Assignee: Institut de Radioprotection et de Surete Nucleaire, Fontenay Aux Roses (FR)

( * ) Notice: Subject to any disclaimer, the term of this patent is extended or adjusted under 35 U.S.C. 154(b) by 170 days.

(21) Appl. No.: 12/746,314

(22) PCT Filed: Dec. 4, 2008

(86) PCT No.: PCT/EP2008/066773
§ 371 (c)(1),
(2), (4) Date: Aug. 3, 2010

(87) PCT Pub. No.: WO2009/071619
PCT Pub. Date: Jun. 11, 2009

(65) Prior Publication Data
US 2010/0294956 A1 Nov. 25, 2010

(30) Foreign Application Priority Data
Dec. 7, 2007 (FR) ..................................... 07 59646

(51) Int. Cl.
*G21G 4/08* (2006.01)
(52) U.S. Cl. .................. 250/252.1; 250/496.1
(58) Field of Classification Search ............... 250/252.1, 250/493.1, 496.1
See application file for complete search history.

(56) References Cited

U.S. PATENT DOCUMENTS

| 4,758,725 | A | 7/1988 | Lecomte et al. |
| 6,770,019 | B1 | 8/2004 | Fritz et al. |
| 7,118,524 | B2 * | 10/2006 | Rivard ............................. 600/3 |

FOREIGN PATENT DOCUMENTS
FR 2 589 058 4/1987

OTHER PUBLICATIONS

Schlaeger, M. et al., "Intercalibration and Intervalidation of In-Vivo Monitors Used for Whole-Body Measurements Within the Framework of a German-Belarussian Project", IRPA 11, pp. 1-6 (May 23, 2004)XP002470666.

Carlan, et al., "New Method of Voxel Phantom Creation: Application for Whole Body Counting Calibration and Perspectives in Individual Internal Dose Assessment", International Conference on Radiation Shielding (ICRS-10)and Thirteenth Topical Meeting on Radiation Protection and Shielding Presentation, pp. 1-16 (May 12, 2004) XP002470667.

* cited by examiner

*Primary Examiner* — Kiet T Nguyen
(74) *Attorney, Agent, or Firm* — Oblon, Spivak, McClelland, Maier & Neustadt, L.L.P.

(57) ABSTRACT

A calibrated radioactive source comprises a container and a material labelled by at least one radionuclide. The labelled material is contained in the container and the container is made of a material that is transparent to the radiation emitted by the at least one radionuclide. The source is characterized in that the labelled material is a self-hardening polymer that is chemically inert relative to the material used for the container and in that the container is a flexible sheath. The calibrated source is placed into a hole of a brick of a tissue-equivalent phantom. An assembly is formed by such a calibrated source and a brick of tissue-equivalent phantom.

11 Claims, 2 Drawing Sheets

CALIBRATED FLEXIBLE RADIOACTIVE SOURCE

TECHNICAL FIELD

The invention relates to a calibrated radioactive source that is flexible and that can for example be used in a tissue-equivalent phantom to perform anthropogammametric measurements.

STATE OF THE PRIOR ART

Anthropogammametry is the direct in vivo measurement of the radioactivity present in the body of an individual, for example following a radioactive contamination.

The measurement method generally used to measure the radioactivity present in the body of an individual consists in quantifying the x and γ radiation emitted by any radionuclides that may be present in said body by means of a detector. However, in order to be able to determine this quantity of radionuclides, it is necessary to calibrate the detector beforehand as a function of the radionuclide considered. To do this, a calibrated source is placed in a physical anthropomorphic phantom. A physical or tissue-equivalent phantom is a substitute reproducing the characteristics of the individual to be studied. It is made from materials having densities and atomic numbers similar to those of human tissues, in such a way that the phantom attenuates the radiation in the same manner as the body of the individual to be considered.

One of the most widely used phantoms is the phantom UP-02T ("IGOR"), which consists in a set of rectangular polyethylene bricks of 0.88 kg and 0.4 kg weight that make it possible to simulate different types of persons, ranging from a child of 10 kg to an adult of 110 kg. Each brick comprises two holes in which are placed solid cylindrical radioactive sources of 6 mm diameter and 163 mm length serving to carry out the calibrations.

The calibrated radioactive sources presently used for the IGOR phantom are made of a powder labelled by a radioactive product and contained in a hard plastic cylindrical tube.

The problem is that these sources, adapted for the IGOR phantom, are no longer manufactured or commercialised and that no equivalent source is currently proposed by French and foreign suppliers of calibrated sources. Calibrated sources that reach the end of their lifetime thus cannot be replaced.

Furthermore, these calibrated radioactive sources have the drawback of being easily breakable, which constitutes a non negligible risk of dispersion of the radioactive material.

In addition, the calibrated sources freely slide in the holes of the bricks of the phantom, which constitutes a risk of falling or shearing of one or more calibrated sources during the handling of the phantom, leading once again to a dispersion of the radioactive material.

The inventors have thus sought to produce a replacement calibrated source that is unbreakable and easily insertable into a hole, for example a hole of a phantom brick, but without possibility of untimely sliding once in place.

DESCRIPTION OF THE INVENTION

This aim is attained thanks to a calibrated radioactive source, comprising a container and a material labelled by at least one radionuclide, said labelled material being contained in the container and said container being made of a material transparent to the radiation emitted by said at least one radionuclide, the source being characterised in that the labelled material is a self-hardening polymer that is chemically inert relative to the material used for the container and in that the container is a flexible sheath.

The invention thus consists in combining a flexible sheath made of a polymer material (for example a silicone sheath) with a self-hardening polymer, inert relative to the material used for the flexible sheath (for example an epoxy resin) and labelled by one or more radioactive product(s) (radionuclides).

In the text, "self-hardening polymer" is taken to mean any polymer that can harden without input of heat.

Moreover, "sheath" is taken to mean an envelope of slender and tubular shape. Advantageously, the sheath has an essentially circular section.

By using a flexible sheath and a labelled self-hardening polymer for filling the sheath, a calibrated radioactive source is obtained that conserves the advantages of the sheath, namely its flexibility, its resistance to impacts and its capacity to recover its initial shape after deformation. Thus, given that the risks of rupture of the sheath are low, the risk of dispersion of the radioactive material included in the self-hardening polymer is, as well, very low. The risks of dispersion of the radioactive material in the environment during the transport and the handling of the calibrated source according to the invention are thus largely reduced.

Moreover, since the source is flexible, it may be used in irregular geometries.

Furthermore, since the flexible sheath is made of a polymer material, it has the advantage of being able to be designed with a specific shape that will allow it, when it is deformed, to be inserted easily into a hole or an orifice, then to remain blocked there while recovering its initial shape.

The container, which was a hard plastic tube in the prior art, is replaced by a flexible sheath in the invention. Advantageously, the flexible sheath is a hollow cylinder of essentially constant diameter, for example a pipe.

Advantageously, the flexible sheath is made of a polymer material, for example silicone elastomer.

Advantageously, the self-hardening polymer of the labelled material is an epoxy resin, for example bisphenol.

Advantageously, the self-hardening polymer of the labelled material comprises 53% of epoxy resin, 32% of hardener and 15% of liquefier, to + or −1%. Advantageously, the epoxy resin is ARALDITE MY 757®, the hardener is ARADUR 850 CH® and the liquefier is a monoethylic ether of ethylene glycol.

Advantageously, the labelled material comprises cobalt 57.

The calibrated radioactive source according to the invention may be used in numerous radioactivity measurement devices. For example, the source may be inserted into a tissue-equivalent phantom to perform anthropogammametric measurements. Thus, another object of the invention is an assembly comprising a brick of a tissue-equivalent phantom and at least one calibrated source as described previously. The brick is a polymer block having one face comprising at least one hole intended to receive said calibrated source. The source is configured so as to have at least one curvature in the direction of its length, the distance between the highest part and the lowest part of the source taken in the direction of its width being equal to the largest internal diameter of said hole, so that the source is in contact with the wall of the hole in at least two contact points and exerts pressure forces directed from the source to the wall at the level of said at least two contact points. For example, for a source having a single curvature extending along its length from one end of the source to the other end, the distance between the highest part and the lowest part of the source taken in the direction of the width is the distance between the apex of the curvature (the thickness of the source being included) and the base of the curvature constituted by a straight line joining the two ends of the source.

Indeed, since the source is flexible, it is configured so that, in its initial shape (non-deformed state), it has at least one curvature, the distance between the highest part and the lowest part of the source taken in the direction of its width being greater than the diameter of the hole and that, in its deformed shape, the distance between the highest part and the lowest part of the deformed source taken in the direction of its width is less than the diameter of the hole in order that the source can be inserted into the hole. On recovering is initial shape, the source is going to exert pressure forces at the level of contact points of the source with the internal wall of the hole. The advantage of the source according to the invention is that, since the source conserves a certain flexibility on account of the use of a flexible sheath, it is possible to deform the source to insert it into the hole of the brick of the phantom. Once inserted into the hole, the source tends to recover its initial shape and is maintained in place by exerting pressure forces at certain points of the internal walls of the hole. Thus, once in place, the calibrated source does not slide: it is self-blocking. Advantageously, the hole of the brick is a cylindrical and rectilinear hole of essentially constant diameter.

Finally, an object of the invention is a method for placing such a calibrated source in a hole of a block. The method for placing a calibrated radioactive source in a hole present in one face of a block, comprises the following steps:

the provision of a calibrated source according to any of claims 1 to 6, said source having at least one curvature over its length, the deformation of the calibrated source until the distance between the highest part and the lowest part of the source taken in the direction of its width is less than the smallest diameter of the hole of the block, the insertion of the source into said hole and the blockage of the source in said hole by return of the source to its non-deformed state, the distance between the highest part and the lowest part of the source taken in the direction of its width in its non-deformed state being greater than the smallest diameter of the hole.

Once placed in the hole, the source tends to recover its initial shape and is maintained in place in the hole while exerting a pressure force at certain points on the internal walls of the hole.

Advantageously, the length of the source is less than or equal to the length of the hole of the block in which it is inserted. The calibrated source thus has dimensions adapted to the dimensions of the hole.

Advantageously, the block is a brick of a tissue-equivalent phantom made of polymer.

BRIEF DESCRIPTION OF DRAWINGS

The invention will be better understood and other advantages and particularities will become clear on reading the following description, given by way of non limiting example, and be referring to the appended figures, among which.

DETAILED DESCRIPTION OF SPECIFIC EMBODIMENTS

Figure 1:
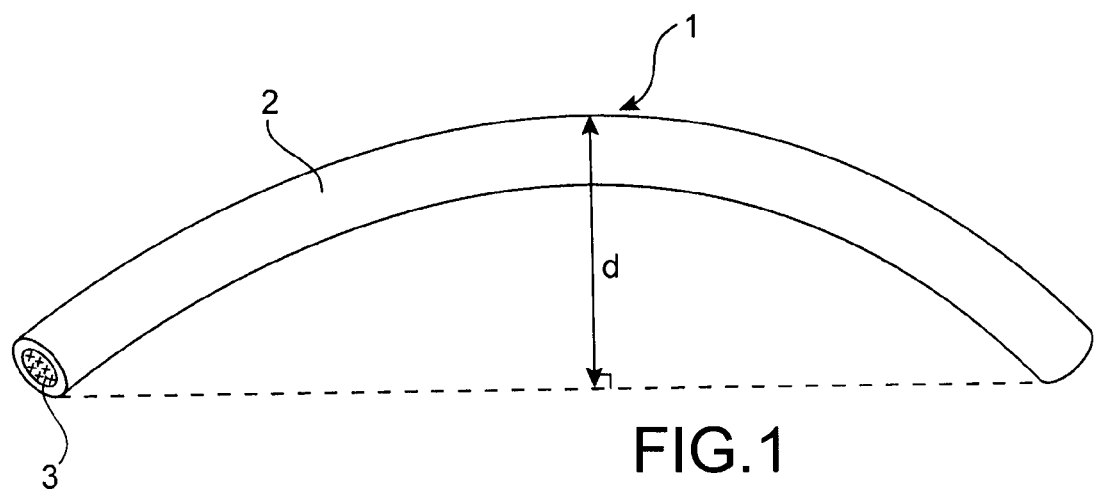
FIG. 1 represents a calibrated source according to the invention.

The calibrated source 1 according to the invention comprises a flexible sheath 2 into which is injected a resin labelled by one or more radionuclides 3 (see FIG. 1). The ends of the sheath are coated with a layer of varnish (not represented) that makes it possible to seal the calibrated source.

Figure 2:
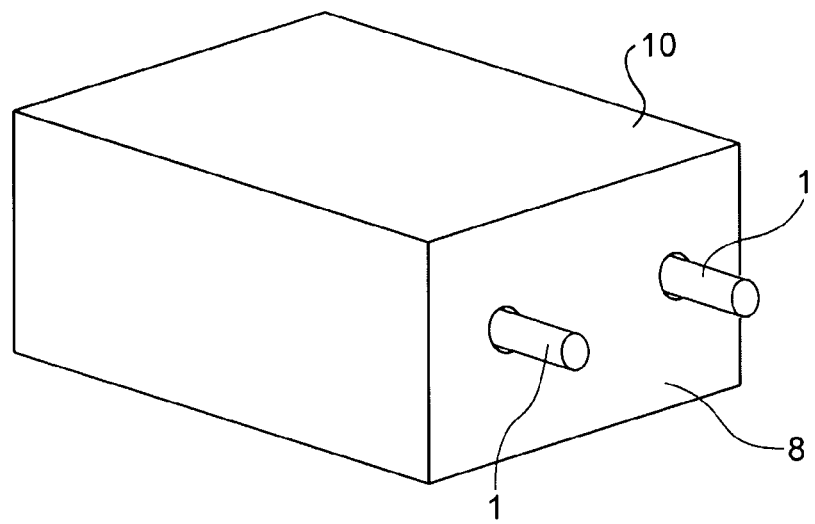
FIG. 2 represents a brick of a phantom into which two calibrated sources according to the invention are being introduced.

This calibrated source 1 may for example be inserted into a brick 10 of a tissue-equivalent phantom. In FIG. 2 is represented such a brick comprising, in one of its faces 8, two orifices into which two calibrated sources are being introduced. In this FIG. 2, it may be seen that the diameter of the source is less than the diameter of the hole.

The calibrated source according to the invention may be obtained by following the following steps:

preparing a calibrated solution comprising at least one radionuclide and preparing a self-hardening polymer, providing a flexible sheath made of material transparent to the radiation emitted by the calibrated solution and resistant to impacts, mixing the calibrated solution and the self-hardening polymer until a homogeneous composition is obtained, filling the flexible sheath with the homogeneous composition, leaving the filled sheath to stand until the complete hardening of the homogeneous composition is obtained, sealing the ends of the flexible sheath.

According to one embodiment, the method of production may further comprise, after the step of leaving the filled sheath to stand and before the sealing step, a step of cutting the flexible sheath into several sections, each constituting a source. This cutting of the filled sheath into several sections makes it possible in the end to obtain, in one go, several calibrated sources. Advantageously, the sections are essentially of same length.

The sealing of the ends of the sheath may be obtained by the application of a varnish on said ends. This makes it possible to seal the calibrated source. It is pointed out that in the case where the sheath is cut into several sections, the sheath then has 2n ends, with n equal to the number of sections and it is these 2n ends that are sealed, for example by the application of a varnish.

Preferably, the calibrated solution has a weight less than or equal to 2% of the weight of the homogeneous composition.

According to one embodiment, the preparation of the self-hardening polymer is carried out by mixing epoxy resin, a hardener and a liquefier. Advantageously, the self-hardening polymer comprises 53% of epoxy resin, 32% of hardener and 15% of liquefier, to + or −1%. Advantageously, the epoxy resin is ARALDITE MY 757®, the hardener is ARADUR 850 CH® and the liquefier is a monoethylic ether of ethylene glycol.

Advantageously, the material of the flexible sheath is a polymer, for example a silicone elastomer.

By way of illustration, the production of ten calibrated sources labelled with cobalt 57 and adapted for anthropogammametric measurement tests in the IGOR tissue-equivalent phantom will be described.

As has been pointed out above, the calibrated source according to the invention comprises a self-hardening polymer labelled by means of at least one radionuclide and contained inside a flexible sheath.

The self-hardening polymer is obtained by mixing three products, namely a resin chemically inert relative to the material used for the sheath, for example a bisphenol A epoxy resin, a hardener and a liquefier. The liquefier makes it possible to ensure the homogenisation of the mixture constituted by the resin, the hardener and the calibrated solution.

In the present example, an epoxy resin commercialised under the brand name ARALDITE MY 757, a hardener commercialised under the brand name ARADUR 850 CH are used, these two products being commercialised by the company HUNTSMAN ADVANCED MATERIALS (EUROPE) BVBA, and the liquefier is for example a monoethylic ether of ethylene glycol, chemically pure, the empirical formula of which is $C_2H_5OCH_2CH_2OH$.

These products are poured successively into a plastic recipient and their weights are determined beforehand by weighing while keeping to the following proportions, expressed in percentage of the total weight of the mixture:

53% of epoxy resin,
32% of hardener,
15% of liquefier,
which corresponds to the following quantities of 15.9 g of epoxy resin MY 757, 9.6 g of hardener 850 CH and 4.5 g of liquefier $C_2H_5OCH_2CH_2OH$.

To this mixture is added 0.19281 g of a calibrated solution of cobalt 57, i.e. 10 420 Bq on the 3 Dec. 2004, obtained by mixing 50 microgrammes of labelled cobalt chloride in 5 mL of 0.1 M hydrochloric acid.

The different components are then mixed until a homogeneous composition is obtained. For example, the components may be mixed manually using a wooden spatula.

It is pointed out the weight of the calibrated solution is quantified by differential weighing and must be less than 2% of the total weight of the homogeneous composition, in other words of the product comprising at the same time the calibrated solution, the elastomer, the hardener and the liquefier. If the calibrated solution is greater than 2% of the total weight of the homogeneous composition, the polymerisation is not homogeneous, which adversely affects the quality of the source.

The homogeneous composition is then introduced into a flexible sheath made of material transparent to the radiation emitted by the radionuclide(s) present in the self-hardening polymer. The sheath is a flexible sheath made of polymer chemically inert relative to its container, in other words the labelled self-hardening polymer. In our example, the silicone sheath used is a cylindrical pipe of essentially constant diameter.

The material of the sheath is chosen so that the sheath has a good resistance to sunlight and ozone, and generally speaking, to all the normal factors of ageing of polymers.

The material of the sheath is also chosen so that the sheath conserves its physical, mechanical and electrical properties in the range of temperatures in which the source will be used; for example, the material of the sheath continuously conserves said properties between −20 and +200° C.

The sheath is for example made of silicone elastomer.

In order to avoid inclusions of air bubbles in the final product, the homogeneous composition is left to stand for a certain time, preferably 1 hour, before carrying out the filling of the flexible sheath. The stand time is chosen so that the labelled self-hardening polymer has sufficiently degassed, but that it has not too much hardened: a waiting time of 1 hour is a good compromise with the type of polymer, hardener and liquefier used in this example.

Then, after having stood for one hour, the homogeneous composition is injected into a flexible sheath of silicone elastomer pipe type measuring two meters long, 5.5 mm external diameter and 3 mm internal diameter, while creating a vacuum in the sheath by means of a peristaltic pump (the pumping rate is adjusted to 7 mL per min). The injection by pumping is stopped when the homogeneous composition reaches around 5 cm from the valve of the peristaltic pump. The filled sheath is then placed on a flat support, if necessary fixing it onto the support, and the two ends of the sheath are raised into vertical position in order to prevent the homogeneous composition from flowing out of the sheath.

The filled sheath is left to stand in order that the homogeneous composition, and in particular the self-hardening polymer that it contains, can degas and harden.

After 72 hours, the hardening of the homogeneous composition is complete: the appearance of the homogeneous composition in the sheath is satisfactory (without bubbles and of homogeneous colour).

The sheath is then cut into ten sections each measuring 163 mm long. The ten sections thus form ten calibrated sources each having a length of 163 mm and an external diameter of 5.5 mm.

Then, the ends of each of the sections are coated with a layer of varnish in order to guarantee the sealing of each calibrated cylindrical source.

Given that the homogeneous composition, once hardened, remains however flexible since it is placed inside a flexible sheath, the source (filled sheath) also conserves a flexible character. Thus, even when the sheath is damaged (which is much rarer than with a tube made of hard plastic), the contents of the sheath (in other words the labelled homogeneous composition) do not flow and do not spread outside of the sheath, unlike the powders of the prior art, which disperse easily. In the end, flexible and sealed radioactive sources are thereby obtained.

These ten sources are then weighed and their radioactivity is measured. To do this, the sources are alternately positioned in the bottom of a plastic box adapted for a gamma spectrometry measurement. The box is placed 5 cm from a gamma detector, which receives and counts the gamma photons coming from the cobalt 57 of the sources (principal line at 122 keV), during a measurement time of 4 200 seconds.

The activity of each source is then determined. To do this, the average weight of an empty sheath of same length is subtracted from the weight of a determined source to obtain the weight of homogeneous composition included in the sheath. The activity is obtained by multiplying the total activity incorporated in the totality of the homogeneous composition by the weight of homogeneous composition present in the sheath in question, and by dividing by the total weight of homogeneous composition prepared.

The results are shown in table 1 below. It is pointed out that a value equal to 3.0028 g has been taken as average weight of the empty sheath.

On reading these results, it may be noted that the calibrated sources according to the invention are substantially identical. The method of production is thus validated.

TABLE 1

| N° of the sheath | Total weight of the calibrated source (g) | Weight of resin (g) | Total number of hits in 4200 seconds | Counting uncertainty in hits | Activity measured on the 20 Mar. 2006 (Bq) | Number of hits per gramme of resin |
|---|---|---|---|---|---|---|
| 1 | 4.4770 | 1.4742 | 10361 | 221.6 | 145.4 | 7028 |
| 2 | 4.4176 | 1.4148 | 9965.2 | 222.9 | 139.9 | 7044 |
| 3 | 4.4643 | 1.4615 | 10403 | 223.7 | 146.0 | 7118 |
| 4 | 4.4795 | 1.4767 | 10388 | 223.3 | 145.8 | 7034 |
| 5 | 4.5534 | 1.5506 | 10445 | 228.4 | 146.6 | 6736 |
| 6 | 4.5408 | 1.5380 | 10663 | 222.9 | 149.3 | 6913 |
| 7 | 4.5501 | 1.5473 | 10606 | 222.9 | 148.8 | 6 855 |
| 8 | 4.5317 | 1.5289 | 10271 | 218.6 | 144.1 | 6718 |
| 9 | 4.5099 | 1.5071 | 10321 | 221.1 | 144.9 | 6848 |
| 10 | 4.5188 | 1.5160 | 10355 | 217.5 | 145.3 | 6830 |
| Average | | 1.5015 | 10375 | | 145.6 | 6736 |
| Standard deviation | | 0.0478 | 175.5 | | 2.459 | |

One of the advantages of calibrated sources according to the invention is that they enable a better security of use, if only during their handling, for example during the insertion of calibrated sources into the bricks of a phantom to perform the calibration of anthropogammametric measurement installations. Indeed, since the calibrated sources are much more resistant to impacts than known sources, the radiation protection is improved during phases of handling and transport of the sources. The sources can easily be handled and moved to the different anthropogammametric measurement installations situated in France, but also abroad, and inter-laboratory tests may thereby be carried out to compare the results obtained in various geographic locations.

Another advantage is that the calibrated source obtained meets the needs expressed by its future user. Indeed, in the example illustrated above, the calibrated solution introduced into the self-hardening polymer is made from cobalt 57. But the self-hardening polymer can certainly contain another radioactive element or several different radionuclides, such as caesium 137, barium 133, cobalt 60, etc.

Similarly, the quantity of radionuclide(s) that it is desired to introduce into the self-hardening polymer, as well as the intensity of its activity, may be chosen.

Moreover, by choosing the external diameter of the flexible sheath, as well as the length of the sheath sections, it is possible to obtain calibrated cylindrical sources having diameters and lengths adapted to the envisaged use.

The calibrated sources according to the invention may thus, for example, be placed in any IGOR phantoms used in existing anthropogammametric measurement installations.

It is also possible to provide to produce calibrated sources intended to be introduced into phantoms having narrower or wider openings than those of the IGOR phantoms.

The sources according to the invention may for example be used to perform inter-comparisons between laboratories.

Furthermore, since the sources according to the invention may be produced with different diameters and lengths, it is possible to use these sources to perform the calibration of measurement installations using other types of phantom than the IGOR phantom, these phantoms having holes of larger or smaller diameters than those of the IGOR phantoms.

The source may have an initial shape (non-deformed state) having one or more curvatures. For example, the source may have a cylinder shape having two curvatures in a plane passing through the axis of the cylinder. By modifying the curvature(s) of the source, it is then possible to insert it into the hole of a phantom. For example, if the hole of the phantom in which it is wished to insert the source is a rectilinear cylinder of constant diameter, the curvature(s) of the source may be attenuated in such a way that the source can be inserted into the hole. Once inserted, the source is going to tend to recover its initial shape and thus remain blocked in the hole.

Figure 3:
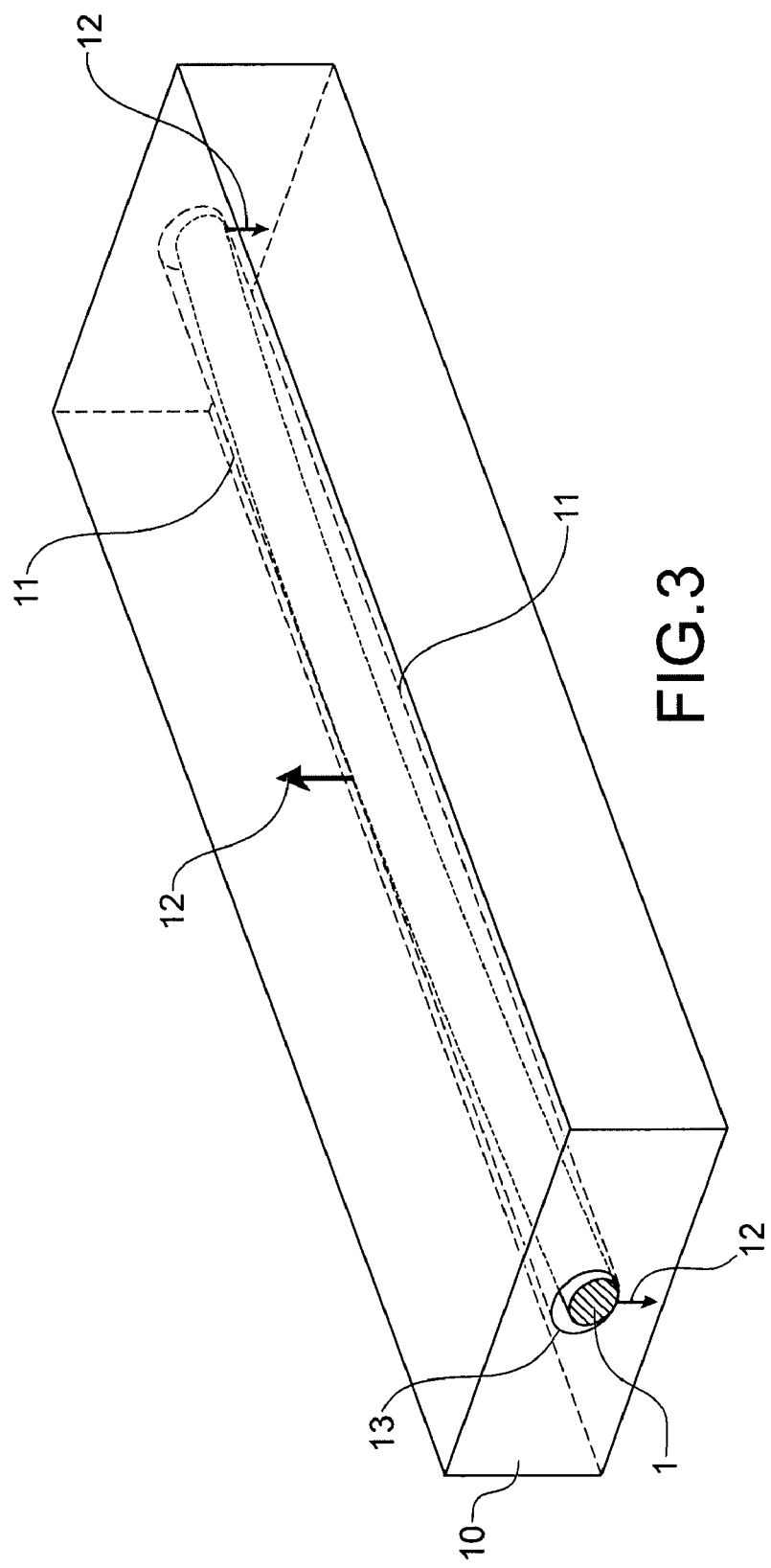
FIG. 3 represents an example of a calibrated source according to the invention inserted into the hole of a phantom brick.

According to an example of application represented in FIG. 1, the source is a cylinder comprising a single curvature extending over the whole length of the source, in other words from one end to the other of the source, the curvature having a deflection greater than the diameter of the hole in which it is desired to introduce the source. The deflection is here the distance between the apex of the curvature, in other words the highest part of the source taken in the direction of its width (the thickness of the source being included in this distance), and the base of the source (straight line passing through the two ends of the source), the distance between the apex and the base being obviously taken along a straight line perpendicular to the base (distance d in FIG. 1). The source is deformed so that the deflection of the curvature is less than the diameter of the hole, then the source is inserted into said hole. Once inserted, the source tends to recover its initial shape in the orifice 13 of the brick. Given that the deflection of the curvature of the source in its initial shape is greater than the diameter of the hole, certain parts of the source are going to come into contact with the walls 11 of the orifice 13 while exerting there pressure forces. As it happens, since the source has a single curvature extending over the assembly of the length of the source, there is in the end three contact points at the level of which are exerted three pressure forces 12 on the internal wall 11 of the orifice, namely two contact points situated at the ends of the lateral surface of the source and at the level of which are exerted two pressure forces directed from the source to the internal wall, and a central contract point at the level of which is exerted a pressure force directed from the source to the internal wall, this latter pressure force being of direction opposite to the direction of the two pressure forces exerted at the ends of the source (see FIG. 3). The source is thus blocked in the hole: it is self-blocking.

By varying the length and the diameter of the source during its production and/or by varying its initial shape (one or more curvatures, more or less pronounced), while taking care however that the source conserves its flexible character, it is thereby possible to form calibrated self-blocking sources that can be easily inserted into the holes of the bricks of any phantom and remain blocked therein.

The invention claimed is:
1. A calibrated radioactive source, comprising a flexible sheath of a container material, and a labeled material labeled by at least one radionuclide, wherein:
the labeled material is contained in the flexible sheath;

at least part of the container material is transparent to radiation emitted by the at least one radionuclide; and at least part of the labeled material is a self-hardening polymer chemically inert relative to the container material.

2. The calibrated radioactive source according to claim 1, wherein the flexible sheath is a hollow cylinder of essentially constant diameter.

3. The calibrated radioactive source according to claim 1, wherein the container material is a polymer material.

4. The calibrated radioactive source according to claim 3, wherein the polymer material is a silicone elastomer.

5. The calibrated radioactive source according to claim 1, wherein the self-hardening polymer of the labelled material is an epoxy type resin.

6. The calibrated radioactive source according to claim 5, wherein the self-hardening polymer comprises 53±1% of epoxy resin, 32±1% of hardener, and 15±1% of liquefier.

7. The calibrated radioactive source according to claim 1, wherein the labelled material comprises cobalt 57.

8. An assembly comprising a brick of a tissue-equivalent phantom and at least one calibrated source according to claim 1, wherein:

the brick is a polymer block, one face of which comprises a hole intended to receive the calibrated radioactive source;

the calibrated radioactive source has at least one curvature along its length, whereby a distance between a highest part and a lowest part of the calibrated radioactive source along its width is equal to a largest internal diameter of the hole; and the calibrated radioactive source is in contact with a wall of the hole in at least two contact points and exerts a force on the wall on level with the at least two contact points.

9. An assembly according to claim 8, wherein the hole is a cylindrical and rectilinear hole of essentially constant diameter.

10. A method for placing a calibrated radioactive source according to claim 1 in a hole on one face of a block, wherein the calibrated radioactive source has at least one curvature along its length, the method comprising:

deforming the calibrated radioactive source until a distance between a highest part and a lowest part of the calibrated radioactive source along its width is less than a smallest diameter of the hole of the block;

inserting the calibrated radioactive source into the hole; and blocking the calibrated radioactive source in the hole by returning the calibrated radioactive source to its non-deformed state, wherein the distance between the highest part and the lowest part of the source along its width in a non-deformed state is greater than the smallest diameter of the hole.

11. The method for placing a calibrated radioactive source in a hole of one face of a block according to claim 10, wherein the block is a brick of a tissue-equivalent phantom of polymer.

\* \* \* \* \*